United States Patent [19]

Niebur

[11] 4,207,637
[45] Jun. 17, 1980

[54] BEEHIVE

[76] Inventor: Mark J. Niebur, Box 753, Malta, Mont. 59538

[21] Appl. No.: 934,698

[22] Filed: Aug. 17, 1978

[51] Int. Cl.² ............................................ A01K 47/00
[52] U.S. Cl. ............................................................. 6/1
[58] Field of Search ........................... 6/1, 2 R, 10, 11; 119/1, 15; 229/90, DIG. 2

[56] References Cited

U.S. PATENT DOCUMENTS

| | | | |
|---|---|---|---|
| 2,023,959 | 12/1935 | Knox | 6/10 |
| 4,055,911 | 11/1977 | Aylor | 119/1 X |

FOREIGN PATENT DOCUMENTS 7314284  4/1974  Netherlands .................... 229/DIG. 2

*Primary Examiner*—Louis G. Mancene
*Assistant Examiner*—Robert P. Swiatek
*Attorney, Agent, or Firm*—Arthur L. Urban

[57] ABSTRACT

A beehive of generally circular configuration including a continuously wound combination of a resilient cellular strip and a plastic strip corrugated transversely of its length, the corrugations being spaced less than about one-half inch and having a depth less than about one-half inch, the wound strip combination being disposed on a common backing surface with one edge of the cellular and plastic strips in contact therewith, and retaining structure maintaining the wound strip combination against the common backing surface.

10 Claims, 3 Drawing Figures

BEEHIVE

This invention relates to a novel beehive and more particularly relates to a novel hive which is especially useful for leaf cutter bees.

The use of bees to pollinate various crops is well known. To ensure that a high degree of cross-pollination is achieved, it is common to place hives for bees in the fields with the growing crops. Cross-pollination with bees which are placed in the fields can produce a major increase in crop yield.

Alfalfa seed growers rely heavily on induced bee pollination to increase the yield of their crop. However, common honey bees cannot be used in the pollination of growing alfalfa. Leaf cutter bees are the only reliable means of cross pollination growing alfalfa. Since approximately 20,000 leaf cutter bees must be placed in each acre of growing alfalfa to achieve optimum pollination, the harvesting and care of the bees is a very important part of the growing of alfalfa seed.

A number of different hives have been proposed for use by alfalfa growers with leaf cutter bees. For example, U.S. Pat. No. 3,191,199 describes a hive formed from grooved wooden boards. When the boards are assembled with the grooves in a matching relationship, a large number of holes or nests are formed. The bees lay their eggs in the passages, seal each passage over and continue in this manner until each passage is filled with eggs and the individual eggs sealed from each other. Generally, the eggs are hatched into larvae by the time the pollination period is completed and the hives are removed from the fields. The hives then are opened and the larvae removed and stored until the next season.

While the grooved board hives were designed to facilitate removal of the larvae, even this construction leaves much to be desired. The hives must be taken apart and the larvae removed from the individual grooves of each board. Then, the boards must be inspected for parasite infestation and if such is found, the boards treated with a parasite killer before reassembling the boards to form the hive again. The boards forming the hive must be reassembled very carefully to avoid unevenness or gaps which may increase the severity of reinfestation by the parasites.

It has been proposed to make disposable hives which can be discarded each season after the larvae have been removed therefrom. This has the advantage that the hives can be torn apart to remove the larvae rather than using care in their removal so the hives can be reused. Unfortunately, this is not a desirable solution since bees prefer to lay their eggs in hives which have been used by them in previous seasons. If new hives are used each year, there will be a lower yield of bee larvae per acre than can be achieved with used hives.

Since bees are in short supply and are not readily available on the open market, alfalfa seed growers go to great efforts to be sure that they obtain maximum yields of bees from their fields. These efforts even include the extra work on their part in the cleaning and assembly of hives by hand. In view of the problems associated with present beehives, however, alfalfa seed growers are very desirous of finding a new type of hive which will reduce the time and labor required for taking apart, cleaning and reassembly of present hives.

The present invention provides a novel beehive which simplifies the cleaning and assembly of the hive components. The beehive of the invention enables the hive to be cleaned and reassembled mechanically with a minimum of hand labor. Also, the hive design facilitates removal of the larvae with a minimum of damage to the larvae and to the hive components. Thus, the beehive of the invention provides high yields of bees in reuseable hives while significantly reducing the work connected with the cleaning of the hives. Further, the design of the beehive reduces parasite infestation. In addition, the design of hive allows the hive components to be treated conveniently during larvae removal to further reduce future parasite infestation. Moreover, the beehive design of the invention permits easy replacement of components during larvae removal. Also, the beehive is simple in design and can be fabricated from commercially available materials relatively inexpensively.

Other benefits and advantages of the novel beehive of the present invention will be apparent from the following description and the accompanying drawings in which.

Figure 1:
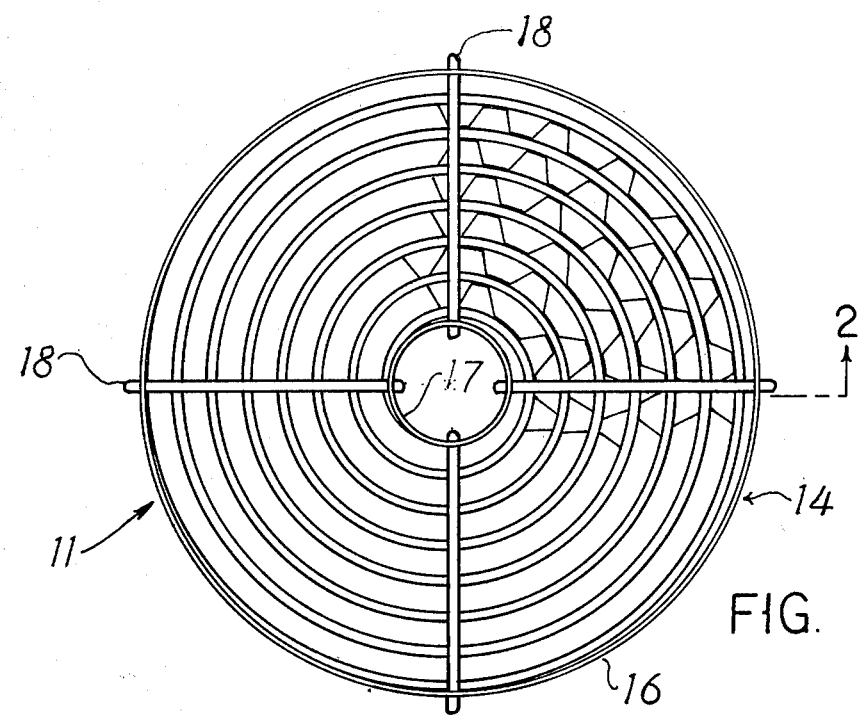
FIG. 1 is a side elevation of one form of the beehive of the invention.
Figure 2:
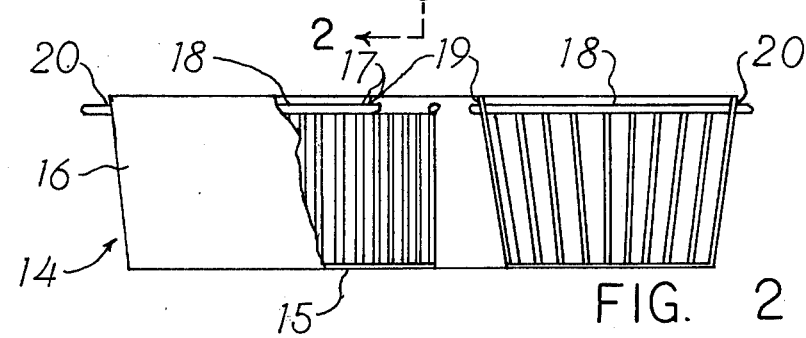
FIG. 2 is a sectional view taken along line 2—2 of FIG. 1.

As shown in the drawings, one form of the novel beehive of the present invention is of a generally circular configuration. The beehive includes a continuously wound combination 11 of a resilient cellular strip 12 and a plastic strip 13. The continuously wound combination of strips 12 and 13 is disposed on a supporting structure 14 with the edges of the strips in contact with a common backing surface 15 thereof. Retaining means are employed to maintain the wound strip combination 11 against the common backing surface 15.

The common backing surface 15 may be a relatively flat surface such as a rigid plastic or wooden sheet or board or the like. The retaining means may be wires, straps or the like which extend across the wound strip combination 11 and are fastened to the backing surface 15.

More advantageously, as shown in the drawings, the supporting structure 14 includes a continuous flange section 16 which extends substantially perpendicularly from the common backing surface 15. Also, it is desirable that the supporting structure 14 include a central core member 17 extending from the backing surface 15. Preferably, the flange section 16 and the central core member 17 are integrally formed or molded with the common backing surface 15. To facilitate assembly and removal of the wound strip combination from the supporting structure 14 as will be described hereinafter, it is advantageous for the peripheral flange section 16 and the central core member 17 to be disposed at a slight diverging angle to that perpendicular to the common backing surface 15, for example, less than about 5°.

The cellular strip 12 and the corrugated plastic strip 13 preferably have a width between about 10% and 20% of the circumference of the wound strip combination 11. For example, a typical hive may have a diameter of about twenty-four inches with a hive thickness or strip width of about four inches. A hive of the above dimensions might have a central core member 17 with a diameter of about three inches. The cellular strip 12 advantageously is a foam strip between about one-eighth and one-half inch in thickness. The foam strip may be formed of a natural or synthetic foam material as desired, with polymeric foams being preferred because of their greater durability and their resistance to parasitic infestation.

The plastic strip 13 as described above is corrugated transversely to its length with the corrugations being spaced less than about one-half inch, that is, the perpendicular straight line distance between the centers of adjacent up and down corrugations. Thus, the distance between the centers of two up corrugations would be considered to be twice the distance between adjacent up and down corrugations. The depth of each corrugation also is less than one-half inch. Preferably, the spacing and the depth of the corrugations are each between about three-sixteenths and three-eighths of an inch.

The plastic strip 13 may be formed of any of the commercially available thermoplastic polymers such as polystyrene, polyolefins, polyamides, polyesters, polyacrylics and the like. Advantageously, the supporting structure 14 including backing surface 15, peripheral flange section 16 and central core member 17 also is molded as a single unit from one of the above plastic materials. Polystyrene is particularly suitable for the fabrication of the plastic strip 13 and the supporting structure 14 because of its low cost, durability, light weight and ease of cleaning.

To assist flange section 16 and central core 17 in retaining the wound strip combination 11 against backing surface 15, a plurality of spoke members 18 extend radially from openings 19 in central core 17. Preferably, spokes 19 extend all the way to the peripheral flange section 16 and through openings 20 therein.

The assembled hive is placed in a field in which bees have been released for pollination of a crop such as alfalfa. The bees deposit eggs in the passages between each cellular strip and the adjoining corrugated plastic strips in the wound strip combination of the hive. When pollination of the field is completed, the hive is removed from the field for cleaning and storage for the next growing season.

Figure 3:
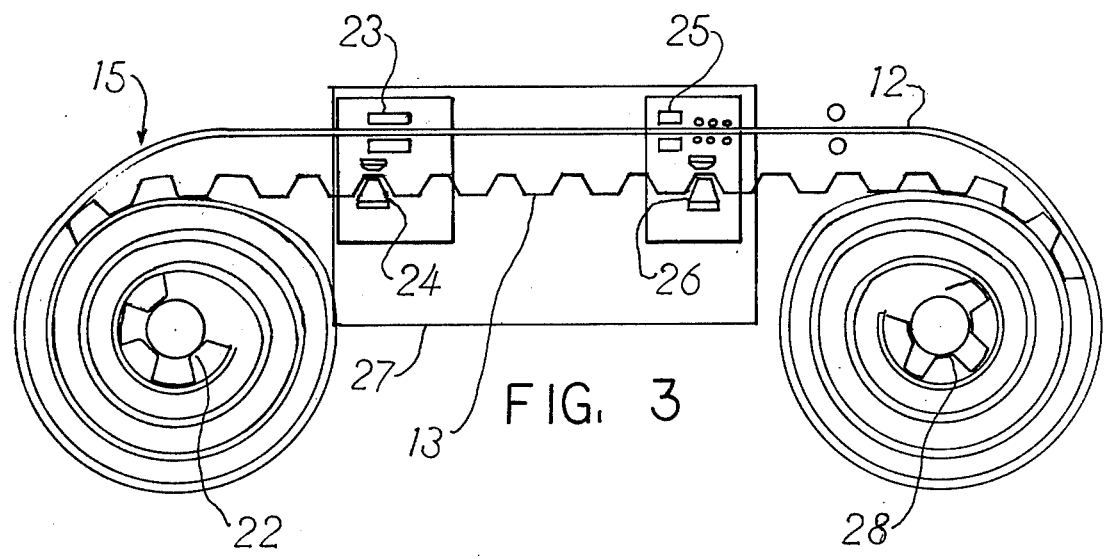
FIG. 3 is a schematic illustration of apparatus for cleaning the beehive shown in FIG. 1.

The beehive of the invention may be cleaned to remove the eggs and larvae simply and conveniently. While this may be accomplished with hand labor, it can be performed more advantageously on apparatus such as shown in FIG. 3. The wound strip combination 11 is removed from the supporting structure 14 by withdrawing spokes 18 from openings 19 and 20 and sliding the strip combination from the supporting structure. The strip combination 11 then is placed on a rotatable shaft 22 and the strips drawn off the roll and separated.

The separated strips 12 and 13 are passed first between brushes 23 and 24 respectively or between other devices (not shown) such as blades, etc. for removal of the eggs and larvae. The eggs and larvae removed from strips 12 and 13 drop into container 27 for storage until they are needed for the next growing season pollination. The strips 12 and 13 then pass through applicators 25 and 26 where materials may be applied to the strips to kill any parasites present and minimize future infestation.

The strips 12 and 13 then are recombined and rewound into a roll as before on a driven shaft 28. If any portions of either strip are damaged and require replacement, this may be accomplished as the strips are being rewound. The damaged portion can be cut from the strip and a new section inserted in its place. The rewound strip combination 11 is reinserted into supporting structure 14 and the retaining spokes 18 placed through openings 19 and 20 again. The beehive then is stored until needed the next season.

The above description and the accompanying drawings show that the present invention provides a novel beehive which can be cleaned and reused simply and conveniently. The design of the beehive of the invention enables the hive to be cleaned and reassembled mechanically with a minimum of hand labor. In addition, the hive design facilitates removal of the larvae with a minimum of damage to the larvae and to the hive components. As a result, the beehive of the invention provides high yields of bees. Since the bee larvae can be removed from the hive easily, the hives can be reused repeatedly.

Another advantage of the novel beehive of the invention is the significant reduction in parasite infestation. Further, the design of the hive permits the hive components to be treated conveniently after larvae removal to further reduce future parasite infestation.

The beehive of the present invention also is simple in design andd can be fabricated from commercially available materials relatively inexpensively. Moreover, the beehive design allows convenient replacement of components during cleaning.

It will be apparent that various modifications may be made in the particular beehive and cleaning apparatus described in detail above and shown in the drawings within the scope of the invention. For example, the size and configuration of the hive may be changed to meet specific requirements. Also, the dimensions of the cellular strip and the corrugated plastic strip may different if desired. Further, the cleaning method and apparatus may be modified to accommodate changes in the hive structure. Therefore, the scope of the invention is to be limited only by the following claims.

What is claimed is:

1. A beehive including a continuously wound combination of a resilient cellular strip and a plastic strip corrugated transversely of its length, said strips not bonded together but being separable and independent of one another, said corrugations being spaced less than about one-half inch apart and having a depth less than about one-half inch, said wound strip combination being disposed on a common backing surface with one edge of said cellular and plastic strips in contact therewith, and retaining means maintaining the structural configuration of said wound strip combination.

2. A beehive according to claim 1 wherein said hive is of a generally circular configuration.

3. A beehive according to claim 1 wherein said retaining means includes a central core member extending from said common backing surface.

4. A beehive according to claim 1 wherein said retaining means includes a peripheral flange section extending from said common backing surface.

5. A beehive according to claim 1 wherein said retaining means includes a central core member and a peripheral flange section extending from said common backing surface at a slightly diverging angle of less than about 5° to the perpendicular.

6. A beehive according to claim 5 wherein said retaining means includes spoke members extending between said central core member and said peripheral flange section.

7. A beehive according to claim 1 wherein said cellular and plastic strips have a width between about 10% and 20% of the circumference of said wound strip combination.

8. A beehive according to claim 1 wherein said cellular strip is a foam strip between about one-eighth and one-half inch in thickness.

9. A beehive according to claim 1 wherein said corrugations are spaced apart between about three-sixteenths and three-eighths inch and have a depth between about three-sixteenths and three-eighths inch.

10. A method of cleaning a beehive including a continuously wound combination of a resilient cellular strip and a plastic strip corrugated transversely of its length, the steps comprising separating said cellular strip from said corrugated plastic strip, cleaning said strips while separated to remove larvae therefrom, recombining said cellular and plastic strips, rewinding said cellular and plastic strips into said wound strip combination.

* * * * *